United States Patent
Schubert et al.

(10) Patent No.: US 8,115,024 B2
(45) Date of Patent: Feb. 14, 2012

(54) PROCESS FOR PREPARING POROUS METAL-ORGANIC FRAMEWORK MATERIALS

(75) Inventors: Markus Schubert, Ludwigshafen (DE); Ulrich Mueller, Neustadt (DE); Michael Hesse, Worms (DE); Uwe Diehlmann, Hassloch (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 569 days.

(21) Appl. No.: 12/278,514

(22) PCT Filed: Feb. 5, 2007

(86) PCT No.: PCT/EP2007/051071
§ 371 (c)(1),
(2), (4) Date: Aug. 6, 2008

(87) PCT Pub. No.: WO2007/090809
PCT Pub. Date: Aug. 16, 2007

(65) Prior Publication Data
US 2009/0042000 A1  Feb. 12, 2009

(30) Foreign Application Priority Data
Feb. 10, 2006  (EP) .................... 06101533

(51) Int. Cl.
*C07F 1/00*  (2006.01)
(52) U.S. Cl. .......... 556/114; 556/115; 428/219
(58) Field of Classification Search ............. 556/114, 556/115; 428/219
See application file for complete search history.

(56) References Cited

FOREIGN PATENT DOCUMENTS
JP           1 070 538       1/2001
WO          02 088148       11/2002
WO         2005 049892      6/2005

OTHER PUBLICATIONS

U.S. Appl. No. 12/668,436, filed Jan. 11, 2010, Schubert, et al.
Wang, Qing M. et al., "Metallo-Organic Molecular Sieve for Gas Separation and Purification", Microporous and Mesoporous Materials, vol. 55, pp. 217-230 (2002).
Sudik, Andrea et al., "Design, Synthesis, Structure, and Gas ($N_2$, Ar, $CO_2$, $CH_4$, and $H_2$) Sorption Properties of Porous Metal-Organic Tetrahedral and Heterocuboidal Polyhedra", J. Am. Chem. Soc., vol. 127, pp. 7110-7118 (2005).
Schlichte, Klaus et al., "Improved Synthesis, Thermal Stability and Catalytic Properties of the Metal-Organic Framework Compound $Cu_3(BTC)_2$", Microporous and Mesoporous Materials, vol. 73, pp. 81-88 (2004).
Chui, Stephen S.-Y. et al., "A Chemically Functionalizable Nanoporous Material $[Cu_3(TMA)_2(H_2O)3]n$", Science, vol. 283, pp. 1148-1150 (1999).
U.S. Appl. No. 12/863,339, filed Jul. 16, 2010, Schubert, et al.
U.S. Appl. No. 12/594,604, filed Oct. 5, 2009, Stein, et al.
U.S. Appl. No. 12/597,616, filed Oct. 26, 2009, Schubert, et al.
U.S. Appl. No. 12/601,022, filed Nov. 20, 2009, Schubert, et al.
U.S. Appl. No. 12/600,539, Nov. 17, 2009, Schubert, et al.

*Primary Examiner* — Porfirio Nazario Gonzalez
(74) *Attorney, Agent, or Firm* — Oblon, Spivak, McClelland, Maier & Neustadt, L.L.P.

(57) ABSTRACT

The present invention relates to a method for producing a porous metal-organic framework material comprising the step
reacting a reaction mixture in the liquid phase of at least one copper compound having at least one at least bidentate, organic compound which can bind by coordination to the copper in the presence of a nonaqueous solvent, the at least one at least bidentate, organic compound being derived from a polycarboxylic acid having at least three carboxyl groups, and the reaction proceeding at atmospheric pressure above 80° C.

11 Claims, No Drawings

PROCESS FOR PREPARING POROUS METAL-ORGANIC FRAMEWORK MATERIALS

The present invention relates to a method for producing porous metal-organic framework materials.

Porous metal-organic framework materials form an interesting class of substances, which can be an alternative to inorganic zeolites for the most varied applications.

Such applications are, for example, in the field of storage, separation or controlled release of chemical substances, such as, for example, gases, or in the field of catalysis. In this case, in particular the porosity of the organic framework material plays a critical role. The pores present in a defined form in the metal-organic framework material firstly increase the specific surface area of the material and make possible selective separation of mixtures. The same applies to materials of this type when they are used as support material in chemical reactions, for example in catalytic reactions.

Metal-organic framework materials are known in the prior art and typically comprise at least one, at least bidentate, organic compound bound by coordination to at least one metal ion. For such framework materials the abbreviation MOF (metal organic framework) is frequently used.

Porous metal-organic framework materials, similarly to organic polymers, have an endless framework which is made up by repeating units.

However, there also exists a group of metal-organic framework materials which are described in the most recent literature as what are termed "restricted" framework materials. By special selection of the organic compound, the framework does not extend endlessly. Rather, development of polyhedra occurs. A. C. Sodic et al., J. Am. Chem. Soc. 127 (2005), 7110-7118 describe, for example, such special framework materials. In this case, to delimit them from polymeric MOF materials, they are termed metal-organic polyhedra (MOP). All these metal-organic framework materials have in common their porosity. Closely linked with the porosity of such materials is their specific surface area which greatly affects their properties. As a measure for characterization of such surfaces, the specific surface area according to Langmuir is to be considered.

Therefore in the production of such materials, in addition to a good yield, also the generation of high specific surface areas in the production is of great importance. This applies in particular to the production of large amounts of framework material.

A particular group of metal-organic framework materials are copper-organic framework materials. Numerous instructions are described in the literature, for example for Cu-organic framework materials where the metal is copper(II) ion and the organic compound is 1,3,5-benzenetricarboxylic acid. In addition, novel Cu-organic framework materials have been produced by the electrochemical route, as described in WO-A 2005/049892.

Q. M. Wang et al., Microporous and Mesoporous Materials 55 (2002), 217-230 describe the production of copper(II)-benzene-1,3,5-tricarboxylate (Cu-BTC) in an ethanol/water mixture using copper nitrate hydrate in the autoclave. In this case specific surface areas of below 1000 $m^2/g$ are obtained.

The experiments described therein for optimization in aqueous solvent systems under hydrothermal conditions and also under reflux also only gives specific surface areas of a little over 1000 $m^2/g$.

K. Schlichte et al., Microporous and Mesoporous Materials 73 (2004), 81-88 describe the production of Cu-BTC in a water/ethanol mixture using copper nitrate hydrate under hydrothermal conditions. Scale-up resulted in the fact that an ideal temperature for hydrothermal conditions is about 120° C.

An ethanol/water mixture is also used in S. S.-Y. Chui et al., SCIENCE 283 (1999), 1148-1150. In this case, likewise, specific surface areas of less than 1000 $m^2/g$ are obtained.

Finally, in EP-A 1 070 538, Cu-BTC is obtained in ethanol under hydrothermal conditions.

All of the above described conventional syntheses have in common the fact that they use low-boiling solvents or water mixtures as solvents and these are employed under hydrothermal conditions together with the required reagents, the copper being used in the form of copper nitrate hydrate.

However, the use of high pressures makes high demands of the synthesis setup for producing a porous metal-organic framework material. Usually, only batch synthesis in comparatively small setups is possible and described. Scale-up proves to be very complex.

In addition, the use of nitrate salts is a problem, in particular at relatively high temperatures, since in this case nitrous gases which are poisonous can be produced.

An object of the present invention is thus to provide methods for producing porous Cu-organic framework materials, such as Cu-BTC, the above described disadvantages being avoided and framework materials being obtained in good yield, in a large amount and having specific surface areas as high as possible.

The object is achieved by a method for producing a porous metal-organic framework material comprising the step reacting a reaction mixture in the liquid phase of at least one copper compound having at least one at least bidentate, organic compound which can bind by coordination to the copper in the presence of a nonaqueous solvent, the at least one at least bidentate, organic compound being derived from a polycarboxylic acid having at least three carboxyl groups, and the reaction proceeding at atmospheric pressure above 80° C.

Surprisingly it has been shown that by means of the above described method framework materials can be produced in comparatively high yield and comparatively high specific surface areas. In addition, easy scale-up is possible, since elevated pressure is not required for the reaction.

The present invention further relates to a porous metal-organic framework material obtainable by the inventive method.

It has proved, inter alia, advantageous if the reaction can be carried out with stirring, which is also advantageous in the event of a scale-up and typically not carried out using solvo- or hydrothermal conditions.

The reaction in the inventive method takes place at atmospheric pressure. Elevated pressure is therefore not necessary for carrying out the reaction. In particular, it is not necessary to employ elevated pressure in order to achieve higher specific surface areas. In particular, it is not necessary to employ solvothermal conditions. Although the reaction is carried out at atmosphere pressure, slight overpressure or reduced pressure can occur due to the apparatus during the reaction. The term "atmospheric pressure" is therefore, in the context of the present invention, to be taken to mean a pressure range which differs from atmosphere pressure at the top and bottom by at most 250 mbar, preferably at most 200 mbar. The actual pressure in the reaction is thus in the above specified range. In addition, preferably, the actual pressure is equal to atmospheric pressure.

The reaction proceeds above 80° C. for the inventive production of a porous metal-organic framework material. In addition, preferably the temperature is in the range from 90°

C. to 150° C., particularly preferably in the range from 100° C. to 130° C., and in particular preferably in the range from 105° C. to 115° C. The temperature should not exceed 200° C., preferably 180° C.

Preferably, the reaction time is 1 to 72 hours, further preferably 2 to 24 hours, and very particularly preferably 3 to 12 hours. However, the reaction can also proceed for a greater time period.

The copper compound used is a copper(I) or copper(II) compound. Preferably it is a copper(II) compound, in particular in the form of a salt.

An advantage of the present invention is that copper(II) nitrate need not be used in its hydrated form, as it is in the prior art.

The present invention therefore relates to a method for producing a porous metal-organic framework material, the copper compound preferably being different from copper(II) nitrate. In particular, it is preferred if one of the hydrates is not used.

Preferably, the copper(II) compound is selected from the group consisting of copper(II) formate, acetate, acetylacetonate, sulfate, bromide, chloride, carbonate and tartrate. Particular preference is given to copper(II) sulfate.

It is further preferred when these copper compounds are used in anhydrous form. This also generally applies to the use of other copper compounds.

The copper compound is reacted with at least one at least bidentate compound which can bind to the copper by coordination. The at least one at least bidentate, organic compound is derived from a polycarboxylic acid having at least three carboxyl groups. The at least three carboxyl groups can, and also further functional groups, in principle be bound to any suitable organic compound, provided that it is ensured that these organic compounds having functional groups are capable of forming the coordinate compound and of producing the framework material.

Preferably, the organic compounds which comprise the at least three functional groups are derived from a saturated or unsaturated aliphatic compound or an aromatic compound, or a compound which is both aliphatic and aromatic.

The aliphatic compound or the aliphatic part of the compound which is both aliphatic and aromatic can be linear and/or branched and/or cyclic, a plurality of cycles per compound also being possible. Further preferably, the aliphatic compound or the aliphatic part of the compound which is both aliphatic and aromatic comprises 1 to 18, further preferably 1 to 14, further preferably 1 to 13, further preferably 1 to 12, further preferably 1 to 11, and in particular preferably 1 to 10, carbon atoms such as, for example, 1, 2, 3, 4, 5, 6, 7, 8, 9 or 10 carbon atoms. In particular preference is given in this case inter alia, to methane, adamantane, acetylene, ethylene or butadiene.

The aromatic compound or the aromatic part of the compound which is both aromatic and aliphatic can have one or else a plurality of nuclei such as, for example, two, three, four or five nuclei, the nuclei being able to be present separated from one another and/or at least two nuclei being able to be present in condensed form. Particularly preferably, the aromatic compound or the aromatic part of the compound which is both aliphatic and aromatic has one, two or three nuclei, one or two nuclei being particularly preferred. Independently of one another, in addition, each nucleus of said compound can comprise at least one heteroatom such as, for example, N, O, S, B, P, Si, preferably N, O and/or S. Further preferably, the aromatic compound or the aromatic part of the compound which is both aromatic and aliphatic comprises one or two $C_6$ nuclei, the two being present either separate from one another or in condensed form.

In particular, aromatic compounds which may be mentioned are benzene, naphthalene and/or biphenyl and/or bipyridyl and/or pyridine.

The term "derive" means, in the context of the present invention, that the at least bidentate, organic compound can be present in the framework material in partially deprotonated or completely deprotonated form. In addition, the at least bidentate, organic compound can comprise further substituents, such as, for example, —OH, —SH, —NH$_2$, —OCH$_3$, —CH$_3$, —NH(CH$_3$), —N(CH$_3$)$_2$, —CN and also halides. Furthermore, the term "derive" means that the carboxyl groups, independently of one another, can be present in the form of their sulfur analogs. Sulfur analogs are the functional groups —C(=O)SH and also the tautomer thereof and —C(=S)SH.

More preferably, the at least one at least bidentate, organic compound is a tricarboxylic or tetracarboxylic acid.

Further more preferably, the at least bidentate, organic compound is an aliphatic or aromatic acyclic or cyclic hydrocarbon having 1-18 carbon atoms which, in addition, has solely at least three carboxyl groups as functional groups.

For example, in the context of the present invention, mention may be made of
tricarboxylic acids such as 2-hydroxy-1,2,3-propanetricarboxylic acid, 7-chloro-2,3,8-quinolinetricarboxylic acid, 1,2,3-, 1,2,4-benzenetricarboxylic acid, 1,2,4-butanetricarboxylic acid, 2-phosphono-1,2,4-butanetricarboxylic acid, 1,3,5-benzenetricarboxylic acid, 1-hydroxy-1,2,3-propanetricarboxylic acid, 4,5-dihydro-4,5-dioxo-1H-pyrrolo[2,3-F]quinoline-2,7,9-tricarboxylic acid, 5-acetyl-3-amino-6-methylbenzene-1,2,4-tricarboxylic acid, 3-amino-5-benzoyl-6-methylbenzene-1,2,4-tricarboxylic acid, 1,2,3-propanetricarboxylic acid or aurintricarboxylic acid,
or tetracarboxylic acids such as
Perylo[1,12-BCD]thiophene 1,1-dioxide-3,4,9,10-tetracarboxylic acid, perylene-tetracarboxylic acids such as perylene-3,4,9,10-tetracarboxylic acid or perylene-1,12-sulfone-3,4,9,10-tetracarboxylic acid, butanetetracarboxylic acids such as 1,2,3,4-butanetetracarboxylic acid or meso-1,2,3,4-butanetetracarboxylic acid, decane-2,4,6,8-tetracarboxylic acid, 1,4,7,10,13,16-hexaoxacyclooctadecane-2,3,11,12-tetracarboxylic acid, 1,2,4,5-benzenetetracarboxylic acid, 1,2,11,12-dodecanetetracarboxylic acid, 1,2,5,6-hexanetetracarboxylic acid, 1,2,7,8-octanetetracarboxylic acid, 1,4,5,8-naphthalenetetracarboxylic acid, 1,2,9,10-decanetetracarboxylic acid, benzophenonetetracarboxylic acid, 3,3',4,4'-benzophenonetetracarboxylic acid, tetrahydrofurantetracarboxylic acid or cyclopentanetetracarboxylic acid such as cyclopentane-1,2,3,4-tetracarboxylic acid.

Very particularly preferably, use is made of if appropriate at least monosubstituted mono-, di-, tri-, tetra- or higher-nuclear aromatic tri- or tetracarboxylic acids, each of the nuclei being able to comprise at least one heteroatom, two or more nuclei being able to comprise identical or different heteroatoms. For example, preference is given to mononuclear tricarboxylic acids, mononuclear tetracarboxylic acids, dinuclear tricarboxylic acids, dinuclear tetracarboxylic acids, trinuclear tricarboxylic acids, trinuclear tetracarboxylic acids, tetranuclear tricarboxylic acids and/or tetranuclear tetracarboxylic acids. Suitable heteroatoms are, for example, N, O, S, B, P; preferred heteroatoms in this case are N, S and/or O. As a suitable substituent in this respect, mention may be made, inter alia, of —OH, a nitro group, an amino group or an alkyl or alkoxy group.

In particular preference, as at least one at least bidentate organic compound, is given to 1,2,3-benzenetricarboxylic acid, 1,2,4-benzenetricarboxylic acid, or 1,3,5-benzenetricarboxylic acid.

In addition to these at least bidentate, organic compounds, the metal-organic framework material can also comprise one or more unidentate ligands.

The metal-organic framework material can occur as polymer or as what is termed "restricted" framework material.

The nonaqueous organic solvent is preferably $C_{4-10}$-alkanol, dimethyl sulfoxide (DMSO), N,N-dimethylformamide (DMF), N,N-diethylformamide (DEF), N,N-dimethylacetamide (DMAc), acetonitrile, toluene, dioxane, chlorobenzene, methyl ethyl ketone (MEK), pyridine, if appropriate halogenated $C_{7-200}$-alkane, sulfolane, alkylene polyols such as ethylene glycol, polyalkylene polyols such as polyethylene glycol, glycerol, propylene carbonate, N-methylpyrrolidone (NMP), gamma-butyrolactone, alicyclic alcohols such as cyclohexanol, ketones such as acetone or acetylacetone, cycloketones such as cyclohexanone, sulfolene or mixtures thereof.

The nonaqueous solvent is selected in such a manner that a reaction temperature of above 80° C. at atmospheric pressure can be achieved. Should the boiling temperature of a solvent or solvent mixture not be sufficiently high, if appropriate adding a higher-boiling solvent can make the desired minimum temperature possible. The reaction mixture is preferably kept below the boiling temperature (under reflux). However, this is not absolutely necessary.

A $C_{4-10}$-alkanol designates an alkyl alcohol having 4 to 10 carbon atoms. Examples of these are n-butanol, isobutanol, tert-butanol, pentanol, hexanol, heptanol, octanol, nonanol, decanol and also mixtures thereof.

An if appropriate halogenated $C_{7-200}$-alkane denotes an alkane having 7 to 200 carbon atoms, with one or a plurality up to all hydrogen atoms being able to be replaced by halogen, preferably chlorine or fluorine, in particular chlorine. Examples of these are heptane, 1,1,1-trichloroheptane, octane, nonane, decane, undecane, dodecane and also mixtures thereof.

Preferred solvents are alkylene polyols, polyalkylene polyols, DMF, DEF and NMP. Particular preference is given to ethylene glycol.

The term "nonaqueous" preferably relates to a solvent which does not exceed a maximum water content of 10% by weight, more preferably 5% by weight, further more preferably 1% by weight, further preferably 0.1%, particularly preferably 0.01% by weight, based on the total weight of the solvent.

Preferably, the total maximum water content of the liquid phase during the reaction is 10% by weight, more preferably 5% by weight, and further more preferably 1% by weight, in particular 0.5% by weight.

The term "solvent" relates to pure solvents and also mixtures of different solvents.

The at least bidentate, organic compound (ligand) can be removed from the pores of the porous metal-organic framework material by treatment of the framework material formed by a nonaqueous solvent. In this case the ligand is removed in a type of "extraction method" and if appropriate replaced in the framework material by a solvent molecule. This gentle method is suitable, in particular, when the ligand is a high-boiling compound.

The treatment is preferably performed for at least 30 minutes, and can, typically, be carried out for up to two days. This can occur at room temperature or elevated temperature. Preferably, this proceeds at elevated temperature, for example at least 40° C., preferably 60° C. Further preferably, the extraction proceeds at the boiling temperature of the solvent used (under reflux).

The treatment can proceed in a simple vessel by slurrying and stirring the framework material. Extraction apparatuses such as Soxhlet apparatuses, in particular industrial extraction apparatuses, can also be used.

As suitable solvents, the abovementioned can be used. However, further solvents can be used. Examples are $C_{1-6}$-alkanol, dimethyl sulfoxide (DMSO), N,N-dimethylformamide (DMF), N,N-diethylformamide (DEF), acetonitrile, toluene, dioxane, benzene, chlorobenzene, methyl ethyl ketone (MEK), pyridine, tetrahydrofuran (THF), ethyl acetate, if appropriate halogenated $C_{1-200}$-alkane, sulfolane, glycol, N-methylpyrrolidone (NMP), gamma-butyrolactone, alicyclic alcohols such as cyclohexanol, ketones such as acetone or acetylacetone, cycloketones such as cyclohexanone, or mixtures thereof.

A $C_{1-6}$-alkanol denotes an alcohol having 1 to 6 carbon atoms. Examples of these are methanol, ethanol, n-propanol, isopropanol, n-butanol, isobutanol, tert-butanol, pentanol, hexanol and also mixtures thereof.

An if appropriate halogenated $C_{1-200}$-alkane denotes an alkane having 1 to 200 carbon atoms, one or more up to all hydrogen atoms being able to be replaced by halogen, preferably chlorine or fluorine, in particular chlorine. Examples of these are chloroform, dichloromethane, tetrachloromethane, dichloroethane, hexane, heptane, octane and also mixtures thereof.

If alternatively, or in addition, the solvent which was used in the reaction is to be removed from the pores, it is preferred that after the reaction the metal-organic framework material formed is treated with a further organic solvent which has a lower boiling point than the nonaqueous organic solvent used in the reaction, to remove from the reaction any at least bidentate compound or nonaqueous organic solvent if appropriate present in the pores of the metal-organic framework material.

Preference is given to solvents or mixtures thereof which have a boiling point at atmospheric pressure below 80° C.

Preference is given in particular to methanol, ethanol, propanol, acetone, MEK and mixtures thereof.

A very particularly preferred extraction solvent is methanol.

The solvent used for extraction can be identical to or different from that for the reaction of the at least one metal compound with the at least one at least bidentate, organic compound. In particular, it is not absolutely necessary in the "extraction", but is preferred, that the solvent is anhydrous.

A drying step can be provided upstream and/or downstream of the extraction. In this case a temperature of 250° C. should not be exceeded.

It is further preferred if during the reaction, water is taken off from the liquid phase. The liquid phase usually comprises the nonaqueous solvents and also water formed in the reaction.

The water can be removed from the reaction mixture in particular by distillation, by stripping or by adsorption media. In the case of stripping (or termed expulsion), components of the liquid phase are removed from the liquid phase by passing through gases and are transferred to a gas phase. Suitable adsorption media are, for example, aluminum oxide, silica gel or a molecular sieve, in particular a 3 Å or 4 Å molecular sieve.

The metal-organic framework materials according to the present invention comprise pores, in particular micropores and/or mesopores. Micropores are defined as those having a diameter of 2 nm or less and mesopores are defined by a diameter in the range from 2 to 50 nm, in each case in accordance with the definition as reported in Pure Applied Chem. 45, page 71, in particular on page 79 (1976). The presence of micropores and/or mesopores can be investigated using adsorption measurements, these measurements defining the uptake capacity of MOFs for nitrogen at 77 Kelvin as specified in DIN 66131 and/or DIN 66134.

As already set forth above, the inventive metal-organic framework materials have a high specific surface area. The specific surface area of the inventive metal-organic framework materials in powder form is preferably greater than 1500 $m^2/g$ according to Langmuir ($N_2$) as specified in DIN 66135 (DIN 66131, 66134). More preferably, the specific surface area is greater than 1700 $m^2/g$, further preferably greater than 1800 $m^2/g$, further preferably greater than 1850 $m^2/g$, and in particular preferably greater than 1900 $m^2/g$.

Framework materials which are present as shaped bodies can have a lower specific surface area.

Preferably, in addition for the inventive porous metal-organic framework material, the pore volume (after determination by $N_2$) is at least 0.5 ml/g, more preferably at least 0.6 ml/g. The preferred mean pore radius (after determination by $N_2$) is preferably between 0.8 and 10 mm, more preferably between 10 and 30 mm.

The metal-organic framework material can be present in pulverulent form or as agglomerate. The framework material can be used as such or it is transformed into a shaped body. Consequently, a further aspect of the present invention is a shaped body comprising an inventive framework material.

Preferred methods for producing shaped bodies in this case are rod extrusion or tableting. In shaped body production, the framework material can have further materials, such as, for example, binders, lubricants or other additives, which are added during the production. Likewise, it is also conceivable that the framework material has further components such as, for example, absorbents such as activated carbon or the like.

With respect to the possible geometries of the shaped bodies, there exist essentially no restrictions. For example, mention may be made of, inter alia, pellets such as, for example, disc-shaped pellets, pills, beads, granules, extrudates such as, for example, rods, honeycombs, meshes or hollow bodies.

For production of these shaped bodies, in principle all suitable methods are possible. In particular preference is given to the following procedures:

kneading/pan-grinding the framework material alone or together with at least one binder and/or at least one pasting agent and/or at least one template compound to obtain a mixture; shaping the resultant mixture by means of at least one suitable method such as, for example, extrusion; optionally washing and/or drying and/or calcining the extrudate; optionally final processing.

Tableting together with at least one binder and/or other aid.

Applying the framework material to at least one if appropriate porous support material. The resultant material can then be further processed in accordance with the above described method to give a shaped body.

Applying the framework material to at least one if appropriate porous substrate.

Kneading/pan-grinding and shaping can proceed according to any suitable method, as described, for example, in Ullmanns Enzyklopädie der Technischen Chemie [Ullmann's Encyclopedia of Industrial Chemistry], 4th edition, volume 2, pp. 313 ff. (1972).

For example, the kneading/pan-grinding and/or shaping can proceed by means of a piston press, roller press in the presence or absence of at least one binder, compounding, pelleting, tableting, extrusion, co-extrusion, foaming, spinning, coating, granulating, preferably spray-granulating, spraying, spray-drying or a combination of two or more of these methods.

Very particularly preferably, pellets and/or tablets are produced.

The kneading and/or shaping can proceed at elevated temperatures such as, for example, in the range from room temperature to 300° C. and/or at elevated pressure such as, for example, in the range from atmospheric pressure up to a few hundred bar and/or in a protective gas atmosphere such as, for example, in the presence of at least one noble gas, nitrogen, or a mixture of two or more thereof.

The kneading and/or shaping is carried out according to a further embodiment with addition of at least one binder, with as binder, in principle use being able to be made of any chemical compound which ensures the viscosity of the mix to be kneaded and/or shaped which is desired for kneading and/or shaping. Consequently, binders in the meaning of the present invention can be not only viscosity-increasing but also viscosity-reducing compounds.

As binders preferred inter alia, mention may be made of, for example, aluminum oxide or aluminum oxide-comprising binders, as are described, for example, in WO 94/29408, silicon dioxide, as described, for example, in EP 0 592 050 A1, mixtures of silicon dioxide and aluminum oxide, as described, for example, in WO 94/13584, clay minerals, as described, for example, in JP 03-037156 A, for example montmorillonite, kaolin, bentonite, halloysite, dickite, nacrite and anauxite, alkoxysilanes, as described, for example, in EP 0 102 544 B1, for example tetraalkoxysilanes such as, for example, tetramethoxysilane, tetraethoxysilane, tetrapropoxysilane, tetrabutoxysilane, or, for example, trialkoxysilanes such as, for example, trimethoxysilane, triethoxysilane, tripropoxysilane, tributoxysilane, alkoxytitanates, for example tetraalkoxytitanates such as, for example, tetramethoxytitanate, tetraethoxytitanate, tetrapropoxytitanate, tetrabutoxytitanate, or, for example, trialkoxytitanates such as, for example, trimethyoxytitanate, triethoxytitanate, tripropoxytitanate, tributoxytitanate, alkoxyzirconates, for example tetraalkoxyzirconates such as, for example, tetramethoxyzirconate, tetraethoxyzirconate, tetrapropoxyzirconate, tetrabutoxyzirconate, or, for example, trialkoxyzirconates such as, for example, trimethoxyzirconate, triethoxyzirconate, tripropoxyzirconate, tributoxyzirconate, silica sols, amphiphilic substances and/or graphites.

As viscosity-increasing compound use can also be made of, for example, if appropriate in addition to the abovementioned compounds, an organic compound and/or a hydrophilic polymer such as, for example, cellulose or a cellulose derivative such as, for example, methylcellulose and/or a polyacrylate and/or a polymethacrylate and/or a polyvinyl alcohol and/or a polyvinylpyrrolidone and/or a polyisobutene and/or a polytetrahydrofuran and/or a polyethyleneoxide.

As pasting agent, use can be made of, inter alia, preferably water or at least one alcohol such as, for example, a monoalcohol having 1 to 4 carbon atoms such as, for example, methanol, ethanol, n-propanol, isopropanol, 1-butanol, 2-butanol, 2-methyl-1-propanol or 2-methyl-2-propanol or a mixture of water and at least one of said alcohols or a polyhydric alcohol such as, for example, a glycol, preferably a water-miscible polyhydric alcohol, alone or as a mixture with water and/or at least one of said monohydric alcohols.

Further additives which can be used for kneading and/or shaping are, inter alia, amines or amine derivatives such as, for example, tetraalkylammonium compounds or amino alcohols and carbonate-comprising compounds such as calcium carbonate. Such further additives are described for instance in EP 0 389 041 A1, EP 0 200 260 A1, or WO 95/19222.

The sequence of the additives such as template compound, binder, pasting agent, viscosity-increasing substance, in the shaping and kneading is in principle not critical.

According to a further preferred embodiment, the shaped body obtained according to kneading and/or shaping is subjected to at least one drying which is generally carried out at a temperature in the range from 20 to 400° C., preferably in the range from 30 to 300° C., and particularly preferably in the range from 80 to 200° C. It is likewise possible to dry in vacuum or under a protective gas atmosphere or by spray drying.

According to a particularly preferred embodiment, in the context of this drying operation, at least one of the compounds added as additive is removed at least in part from the shaped body.

The present invention further relates to the use of the inventive porous metal-organic framework material for taking up at least one substance for its storage, separation, controlled release or chemical reaction and also as support material.

The at least one substance can be a gas or a liquid. Preferably the substance is a gas.

In the context of the present invention, for simplicity the terms "gas" and "liquid" are used, but in this case likewise gas mixtures and also liquid mixtures or liquid solutions are to be understood under the term "gas" or "liquid".

Preferred gases are hydrogen, hydrocarbons, in particular methane, ethane, ethene, acetylene, propane, n-butane and also isobutane, carbon monoxide, carbon dioxide, nitrogen oxides, oxygen, sulfur oxides, halogens, halogenated hydrocarbons, $NF_3$, $SF_6$, ammonia, boranes, phosphanes, hydrogen sulfide, amines, formaldehyde, noble gases, in particular helium, neon, argon, krypton and also xenon.

In particular preference is given to the use for separation of gas mixtures, for example by pressure- or temperature-swing adsorption.

The at least one substance, however, can also be a liquid. Examples of such a liquid are disinfectants, inorganic or organic solvents, motive power fuels, in particular gasoline or diesel, hydraulic fluid, coolant liquid, brake fluid or an oil, in particular machine oil. In addition, the liquid can be halogenated aliphatic or aromatic, cyclic or acyclic hydrocarbon or mixtures thereof. In particular, the liquid can be acetone, acetonitrile, aniline, anisole, benzene, benzonitrile, bromobenzene, butanol, tert-butanol, quinoline, chlorobenzene, chloroform, cyclohexane, diethylene glycol, diethyl ether, dimethylacetamide, dimethyl-formamide, dimethyl sulfoxide, dioxane, glacial acetic acid, acetic anhydride, ethyl acetate, ethanol, ethylene carbonate, ethylene dichloride, ethylene glycol, ethylene glycol dimethyl ether, formamide, hexane, isopropanol, methanol, methoxypropanol, 3-methyl-1-butanol, methylene chloride, methyl ethyl ketone, N-methylformamide, N-methylpyrrolidone, nitrobenzene, nitromethane, piperidine, propanol, propylene carbonate, pyridine, carbon disulfide, sulfolane, tetrachloroethene, carbon tetrachloride, tetrahydrofuran, toluene, 1,1,1-trichloroethane, trichloroethylene, triethylamine, triethylene glycol, triglyme, water or mixtures thereof.

In addition, the at least one substance can be an odor substance.

Preferably, the odor substance is a volatile organic or inorganic compound which comprises at least one of the elements nitrogen, phosphorus, oxygen, sulfur, fluorine, chlorine, bromine or iodine, or an unsaturated or aromatic hydrocarbon, or a saturated or unsaturated aldehyde, or a ketone. More preferred elements are nitrogen, oxygen, phosphorus, sulfur, chlorine, bromine; in particular preference is given to nitrogen, oxygen, phosphorus and sulfur.

In particular, the odor substance is ammonia, hydrogen sulfide, sulfur oxides, nitrogen oxides, ozone, cyclic or acyclic amines, thiols, thioethers and also aldehydes, ketones, esters, ethers, acids or alcohols. Particular preference is given to ammonia, hydrogen sulfide, organic acids (preferably acetic acid, propionic acid, butyric acid, isobutyric acid, valeric acid, isovaleric acid, caproic acid, heptylic acid, lauric acid, pelargonic acid) and also cyclic or acyclic hydrocarbons which comprise nitrogen or sulfur and also saturated or unsaturated aldehydes, such as hexanal, heptanal, octanal, nonanal, decanal, octenal or nonenal and, in particular, volatile aldehydes such as butyraldehyde, propionaldehyde, acetaldehyde and formaldehyde and in addition motive power fuels such a gasoline, diesel (components).

The odor substances can also be olfactory substances which are used, for example, for production of perfumes. Examples which may be mentioned as olfactory substances or oils which release such olfactory substances are: essential oils, basil oil, geranium oil, mint oil, ylang ylang oil, cardamon oil, lavender oil, peppermint oil, muscat oil, camomile oil, eucalyptus oil, rosemary oil, lemon oil, lime oil, orange oil, bergamot oil, muscatel sage oil, coriander oil, cypress oil, 1,1-dimethoxy-2-pherylethane, 2,4-dimethyl-4-phenyltetrahydrofuran, dimethyltetrahydrobenzaldehyde, 2,6-dimethyl-7-octen-2-ol, 1,2-diethoxy-3,7-dimethyl-2,6-octadiene, phenylacetaldehyde, rose oxide, ethyl 2-methylpentanoate, 1-(2,6,6-trimethyl-1,3-cyclohexadien-1-yl)-2-buten-1-one, ethylvanillin, 2,6-dimethyl-2-octenol, 3,7-dimethyl-2-octenol, tert-butyl cyclohexylacetate, anisyl acetate, allyl cyclohexyloxyacetate, ethyllinalool, eugenol, coumarin, ethyl acetoacetate, 4-phenyl-2,4,6-trimethyl-1,3-dioxane, 4-methylene-3,5,6,6-tetramethyl-2-heptanone, ethyl tetrahydrosafranate, geranylnitril, cis-3-hexen-1-ol, cis-3-hexenyl acetate, cis-3-hexenyl methylcarbonate, 2,6-dimethyl-5-hepten-1-al, 4-(tricyclo[5.2.1.0]decylidene)-8-butanal, 5-(2,2,3-trimethyl-3-cycipentenyl)-3-methylpentan-2-ol, p-tert-butyl-alpha-methylhydrocinnamaldehyde, ethyl [5.2.1.0]tricyclodecanecarboxylate, geraniol, citronellol, citral, linalool, linalyl acetate, Ionones, phenylethanol or mixtures thereof.

In the context of the present invention, a volatile odor substance preferably has a boiling point or boiling point range of below 300° C. More preferably, the odor substance is a readily volatile compound or mixture. In particular preferably, the odor substance has a boiling point or boiling range of below 250° C., more preferably below 230° C., in particular preferably below 200° C.

Preference is likewise given to odor substances which have a high volatility. As a measure of the volatility, the vapor pressure can be used. In the context of the present invention a volatile odor substance preferably has a vapor pressure of greater than 0.001 kPa (20° C.). More preferably, the odor substance is a readily volatile compound or mixture. In particular, preferably, the odor substance has a vapor pressure of greater than 0.01 kPa (20° C.), more preferably a vapor pressure of greater than 0.05 kPa (20° C.). Particularly preferably, the odor substances have a vapor pressure of greater than 0.1 kPa (20° C.).

EXAMPLES

Example 1

Production of Cu-1,3,5-BTC-MOF in Ethylene Glycol 12.2 g of 1,3,5-BTC and 13.9 g of anhydrous copper sulfate are suspended in 275 g of ethylene glycol and are kept at 110°

C. with stirring for 8 h. The blue precipitate is filtered off and washed with 5×120 ml of methanol. After drying for 24 h at 75° C. in vacuum (0.2 bar), 6.7 g of product are obtained.

Before the surface area determination, the sample was additionally evacuated at 110° C. The $N_2$ surface area is only 2031 $m^2/g$ (Langmuir).

Example 2

Production of a Cu-1,3,5-BTC-MOF on the Pilot Scale (Scale-Up)

27.8 kg of anhydrous $CuSO_4$ are suspended together with 12.84 kg of 1,3,5-benzenetricarboxylic acid in 330 kg of ethylene glycol and blanketed with $N_2$. The vessel is brought to 110° C. and the synthesis mixture is kept at this temperature for 12 h with stirring. The solution is cooled to 50° C. and filtered under $N_7$ blanketing with a pressure filter. The filter cake is washed with 4×50 l of methanol and blown dry with nitrogen for 96 h.

Two batches were produced. In the first batch, 17 kg of material were present and in the second 14.5 kg. Before the surface area determination, the sample was evacuated at 110° C. in each case for 2 h. The $N_2$ surface area is 2096 and 2073 $m^2/g$ (Langmuir). The XRD of batch 2 is shown in Fig. 1. The pore volume (determined by $N_2$ for fraction <5912 Å) is determined as 0.65 ml/g. The mean pore diameter is 20 Å.

Example 3

Production of a Cu-1,3,5-BTC-MOF 244.2 kg of $CuSO_4$ pentahydrate are suspended together with 73.8 kg of 1,3,5-benzenetricarboxylic acid in 2200 kg of ethylene glycol and blanketed with $N_2$. The vessel is brought to 110° C. and the synthesis mixture is kept at this temperature for 15 h with stirring. The solution is filtered at 110° C. under $N_2$ blanketing with a pressure filter. The filtercake is washed with 2×200 l of methanol and 2×240 l of methanol with stirring. The product is subsequently dried in vacuum at 140° C. for 8 h.

The yield is 46.8 kg. The $N_2$ surface area is 2042 $m^2/g$ (Langmuir).

Example 4

Production of a Cu-1,3,5-BTC-MOF 150 kg of anhydrous $CuSO_4$ are suspended together with 71 kg of 1,3,5-benzene-tricarboxylic acid in 2200 kg of ethylene glycol and blanketed with $N_2$. The vessel is brought to 110° C. and the synthesis mixture is kept at this temperature for 15 h with stirring. The solution is filtered at 110° C. under $N_2$ blanketing with a pressure filter. The filtercake is washed with 2×200 l of methanol and 3×240 l of methanol with stirring. The product is subsequently dried in vacuum at 104° C. for 10 h.

The yield is 61.1 kg. The $N_2$ surface area is 2064 $m^2/g$ (Langmuir).

Comparative Example 5

Solvothermal Production of Cu-1,3,5-BTC-MOF 14.73 g of 1,3,5-BTC in 75 ml of ethylene glycol and 32.6 of $Cu(NO_3)_2.2.5H_2O$ in 75 ml of $H_2O$ are kept at 110° C. together in a Teflon liner for 18 h. On opening, nitrous gases escape. The precipitate is filtered off, washed with water and dried in vacuum at 100° C. for 16 h.

Before the surface area determination the sample is additionally evacuated at 80° C. The $N_2$ surface area is only 793 $m^2/g$ (Langmuir).

Comparative Example 6

Unpressurized Production of a Cu-1,3,5 in a Low-Boiling Solvent Mixture 24.4 g of 1,3,5-BTC and 54.3 g of $Cu(NO_3)_2.2.5H_2O$ are suspended in 125 g of water and 98.5 g of ethanol and kept unpressurized at 84° C. under reflux with stirring for 24 h. The blue precipitate is filtered off and washed with 5×400 ml of water. After drying for 16 h at 110° C., 16.24 g of product are obtained.

Before the surface area determination the sample was additionally evacuated at 100° C. The $N_2$ surface area is only 640 $m^2/g$ (Langmuir).

Example 7

Production of Cu-1,3,5-BTC, Washing with Acetone

A Cu-1,3,5-BTC-MOF is synthesized as in Example 1, but half of the filter cake is washed with 5×100 ml of acetone.

Before the surface area determination the samples were additionally evacuated at 110° C. The $N_2$ surface area of the acetone-washed half, however, was only 1541 $m^2/g$ (Langmuir), that of the MeOH-washed fraction 1940 $m^2/g$.

The invention claimed is:

1. A method for producing a porous metal-organic framework material comprising
    reacting in the liquid phase a reaction mixture of at least one copper compound having at least one at least bidentate, organic compound capable of binding by coordination to the copper in the presence of a nonaqueous solvent, the at least one at least bidentate, organic compound being derived from a polycarboxylic acid having at least three carboxyl groups, wherein the reaction proceeds at atmospheric pressure above 80° C.

2. The method according to claim 1, wherein the reaction proceeds with stirring.

3. The method according to claim 1, wherein the copper compound is different from copper(II) nitrate.

4. The method according to claim 1, wherein the copper compound is selected from the group consisting of copper(II) formate, acetate, acetylacetonate, sulfate, bromide, chloride, carbonate and tartrate, and the same compounds in anhydrous form.

5. The method according to claim 1, wherein the at least one at least bidentate, organic compound is a tricarboxylic or tetracarboxylic acid.

6. The method according to claim 5, wherein the at least one at least bidentate, organic compound is selected from the group consisting of 1,2,3-benzenetricarboxylic acid, 1,2,4-benzenetricarboxylic acid and 1,3,5-benzenetricarboxylic acid.

7. The method according to claim 1, wherein the nonaqueous solvent is selected from the group consisting of $C_{4-10}$-alkanol, dimethyl sulfoxide (DMSO), N,N-dimethylformamide (DMF), N,N-diethylformamide (DEF), N,N-dimethylacetamide (DMAc), acetonitrile, toluene, dioxane, chlorobenzene, methyl ethyl ketone (MEK), pyridine, halogenated $C_{7-200}$-alkane, sulfolane, alkylene polyols, polyalkylene polyols, glycerol, N-methylpyrrolidone (NMP), gamma-butyrolactone, alicyclic alcohols, ketones, cycloketones, sulfolene and mixtures thereof.

8. The method according to claim 1, wherein the liquid phase during the reaction has a maximum water content of 10% by weight.

9. The method according to claim 1, wherein water is taken off from the liquid phase during the reaction.

10. The method according to claim 1, wherein the reaction proceeds in a range of from 90° C. to 150° C.

11. The method according to claim 1, wherein, after the reaction, the metal-organic framework material formed is treated with a further organic solvent which has a lower boiling point than the nonaqueous organic solvent in order to remove from the material any at least bidentate compound or nonaqueous organic solvent present in the pores of the metal-organic framework material.

* * * * *

UNITED STATES PATENT AND TRADEMARK OFFICE
CERTIFICATE OF CORRECTION

PATENT NO. : 8,115,024 B2
APPLICATION NO. : 12/278514
DATED : February 14, 2012
INVENTOR(S) : Markus Schubert et al.

It is certified that error appears in the above-identified patent and that said Letters Patent is hereby corrected as shown below:

In the Specifications:

Column 11, line 25 "The XRD of batch 2 is shown in Fig. 1." should be deleted as there is no Fig. 1 is the patent.

Signed and Sealed this
Thirtieth Day of April, 2013

Teresa Stanek Rea
*Acting Director of the United States Patent and Trademark Office*